United States Patent
Reinmuller et al.

(10) Patent No.: US 10,022,394 B2
(45) Date of Patent: Jul. 17, 2018

(54) ANTIINFECTIVE COMPOSITION

(76) Inventors: Johannes Reinmuller, Weisbaden (DE); Kay Dirting, Wiesbaden (DE)

(*) Notice: Subject to any disclaimer, the term of this patent is extended or adjusted under 35 U.S.C. 154(b) by 19 days.

(21) Appl. No.: 14/124,789

(22) PCT Filed: Jun. 8, 2012

(86) PCT No.: PCT/EP2012/060942
§ 371 (c)(1),
(2), (4) Date: Dec. 9, 2013

(87) PCT Pub. No.: WO2012/168462
PCT Pub. Date: Dec. 13, 2012

(65) Prior Publication Data
US 2014/0113881 A1 Apr. 24, 2014

(30) Foreign Application Priority Data

Jun. 10, 2011 (DE) .................. 10 2011 077 393

(51) Int. Cl.
| A61K 31/727 | (2006.01) |
|---|---|
| A61K 31/728 | (2006.01) |
| A61K 31/726 | (2006.01) |
| A61K 45/06 | (2006.01) |
| A61K 31/405 | (2006.01) |
| A61K 31/60 | (2006.01) |
| A61K 31/737 | (2006.01) |
| C08B 37/08 | (2006.01) |
| C08B 37/00 | (2006.01) |
| C08L 5/08 | (2006.01) |
| A61K 31/738 | (2006.01) |

(52) U.S. Cl.
CPC .......... *A61K 31/728* (2013.01); *A61K 31/405* (2013.01); *A61K 31/60* (2013.01); *A61K 31/726* (2013.01); *A61K 31/727* (2013.01); *A61K 31/737* (2013.01); *A61K 31/738* (2013.01); *A61K 45/06* (2013.01); *C08B 37/003* (2013.01); *C08B 37/0069* (2013.01); *C08B 37/0072* (2013.01); *C08B 37/0075* (2013.01); *C08L 5/08* (2013.01); *C08L 2205/02* (2013.01)

(58) Field of Classification Search
CPC .. C08B 37/0072; A61K 31/727; A61K 31/738
See application file for complete search history.

(56) References Cited

U.S. PATENT DOCUMENTS

| 2,637,724 A | 5/1953 | Jarowski et al. |
|---|---|---|
| 4,465,666 A * | 8/1984 | Lukas .................. A61K 9/0014 424/642 |
| 4,713,448 A | 12/1987 | Balazs et al. |
| 5,099,013 A | 3/1992 | Balazs et al. |
| 5,114,957 A * | 5/1992 | Hendler ................ A61K 31/355 514/356 |
| 5,250,519 A | 10/1993 | Conrad et al. |
| 5,411,874 A * | 5/1995 | Ellwood .................. C12P 19/26 435/101 |
| 5,430,026 A | 7/1995 | Hertel et al. |
| 5,430,133 A | 7/1995 | Piani et al. |
| 5,563,051 A | 10/1996 | Ellwood et al. |
| 6,166,007 A | 12/2000 | Sodemann |
| 6,302,108 B1 * | 10/2001 | Levine ................. A61K 31/549 128/830 |
| 6,423,706 B2 | 7/2002 | Sodemann |
| 6,498,157 B2 | 12/2002 | Sodemann |
| 6,498,246 B1 | 12/2002 | Usuki et al. |
| 6,569,852 B1 | 5/2003 | Sodemann |
| 7,807,656 B2 | 10/2010 | Reinmueller |
| 7,902,171 B2 | 3/2011 | Reinmueller |
| 8,178,658 B2 | 5/2012 | Crouse et al. |
| 2001/0003746 A1 | 6/2001 | Sodemann |
| 2002/0111346 A1 | 8/2002 | Sodemann |
| 2005/0187185 A1 * | 8/2005 | Reinmuller ............ A61K 47/36 514/54 |
| 2006/0029571 A1 * | 2/2006 | Karageozian et al. .... 424/78.38 |
| 2006/0229356 A1 * | 10/2006 | Santoro ................ A61K 31/315 514/420 |
| 2007/0275955 A1 * | 11/2007 | Pfirrmann ............ A61K 31/541 514/222.5 |
| 2008/0177217 A1 * | 7/2008 | Polaschegg .................. 604/6.16 |
| 2008/0188441 A1 * | 8/2008 | Reinmuller .......... A61K 31/728 514/54 |
| 2009/0209476 A1 | 8/2009 | Crouse et al. |

(Continued)

FOREIGN PATENT DOCUMENTS

| AU | 664096 B2 | 11/1995 |
|---|---|---|
| DE | 19606897 A1 | 8/1997 |

(Continued)

OTHER PUBLICATIONS

Matsuno, H. et al "A new antibacterial carrier of hyaluronic acid gel" J. Orthrop. Sci. (2006) vol. 11, pp. 497-504.*
Chromik, A. et al "Gene expression analysis of cell death . . . " BMC Cancer (2010) vol. 10, pp. 1-13.*
Neary, P. et al "The evolving role of taurolidine . . . " Ann. Surg. Oncol. (2010) vol. 17, pp. 1135-1143.*
No, J. et al "Human papillomavirus vaccine . . . " Molec. Carcinogen. (2011) vol. 50, pp. 244-253.*
Shukla, S. et al "Infection of human papillomaviruses in cancers . . . " Indian J. Med. Res. (2009) vol. 130, pp. 222-233.*

(Continued)

*Primary Examiner* — Leigh C Maier
(74) *Attorney, Agent, or Firm* — Millen, White, Zelano, Branigan, P.C.

(57) ABSTRACT

The present invention relates to the use of hydroxymethyl-group-containing glycosaminoglycans, such as in particular hydroxymethyl-hyaluronic acid, for the treatment and prevention of infectious diseases or malignant or premalignant diseases, in particular of the skin or mucosa. The invention additionally provides a preparation method for glycosaminoglycans modified with hydroxymethyl groups.

18 Claims, No Drawings

(56) References Cited

U.S. PATENT DOCUMENTS

| | | | |
|---|---|---|---|
| 2012/0122805 A1 | 5/2012 | Crouse et al. | |
| 2012/0172218 A1 | 7/2012 | Crouse et al. | |

FOREIGN PATENT DOCUMENTS

| | | | |
|---|---|---|---|
| DE | 10209966 A1 | 5/2003 | |
| DE | 69931159 T2 | 2/2007 | |
| EP | 1837347 A1 | 9/2007 | |
| KR | 102010092843 A | 8/2010 | |
| WO | 90/04607 A2 | 5/1990 | |
| WO | 92/08799 A1 | 5/1992 | |
| WO | 00/01391 A1 | 1/2000 | |
| WO | 2003041723 | 5/2003 | |
| WO | 2005067944 | 7/2005 | |
| WO | 2009102736 A1 | 8/2009 | |

OTHER PUBLICATIONS

De Flora, S. et al "The prevention of infection-associated cancers" Carcinogen. (2011) vol. 32, No. 6, pp. 787-795.*

International Search Report from PCT/EP2012/060942 dated Aug. 14, 2012.

Jeannin Jean Francois et al. "Antitumor Effect of Synthetic Derivatives of lipid A in an Experimental model of Colon in the Rat" Gastroenterology, Elsevier, vol. 101, No. 3, [1991], pp. 726-733. Cancer.

Jacek Dutkiewicz, et al. "Some Aspects of the Reaction between Chitosan and Formaldehyde" Journal of Macromolecular Science: Part A—Chemistry, A20(8), [1983], pp. 877-885.

Payman Pirnazar et al. "Bacteriostatic Effects of Hyaluronic Acid" J. Periodontol, [Apr. 1999], vol. 70, No. 4, 5 pages.

Payman Pimazar et al., "Bacteriostatic Effects of Hyaluronic Acid", vol. 70, No. 4, Apr. 1999, pp. 374.

* cited by examiner

ANTIINFECTIVE COMPOSITION

The present invention relates to the use of hydroxymethyl-group-containing glycosaminoglycans, such as in particular hydroxymethyl-hyaluronic acid, for the treatment and prevention of infectious diseases or malignant or premalignant diseases, in particular of the skin or mucosa. The invention additionally provides a preparation method for glycosaminoglycans modified with hydroxymethyl groups.

Infectious diseases are diseases caused by pathogens such as viruses, bacteria or fungi, and they exhibit a broad spectrum of progressions over time and of symptoms, which are often specific to the pathogen. Infection takes place by contact of an organism with a pathogen, the infection paths being characteristic for the disease and its pathogen. Medicine provides specific counter-agents for many diseases that are caused by pathogens, such as antibiotics against bacteria, antimycotics against fungi and virostatics against viruses. There is additionally the possibility of preventive inoculation against some pathogens.

However, some infectious diseases still cannot be cured today. In addition, there is the problem of the development of resistance of the various active ingredients used to control the pathogens. Resistance is understood as meaning the acquired resistance of a pathogen to an active ingredient. For example, in the case of resistant bacterial strains, treatment with a particular antibiotic or even with several antibiotics no longer leads to the desired death thereof or inhibition of the growth thereof. Research is therefore being intensively concentrated also on the development of therapeutic agents against resistant pathogens.

A further problem is secondary infections, in which, in addition to an infection that was present initially (primary infection), a further infection with a different pathogen occurs. Such a further infection occurring after a primary infection can present considerable problems for the immune system and also make therapy and medication difficult. Secondary infections with viral, bacterial or fungal diseases are of particular importance, when the primary infection is already associated with a weakening of the immune system. It would therefore be desirable to provide active ingredients which enable different pathogens to be controlled simultaneously.

Against this background, the object of the present invention was to provide a possibility for treating or preventing infectious diseases. Of particular interest in this context is the provision of an agent which can be used for the treatment of different infectious diseases caused by different pathogens, such as viruses, bacteria or fungi.

Surprisingly, it has been found that glycosaminoglycan derivatives which have been modified with hydroxymethyl groups possess an excellent anti-infective action against different types of pathogens. It has been found that this anti-infective action is attributable to the presence of hydroxymethyl groups on the glycosaminoglycan.

Accordingly, the invention provides a hydroxymethyl-group-containing glycosaminoglycan for use in the treatment or prevention of infectious diseases or malignant or premalignant diseases.

The invention further provides a method for preventing or treating an infectious disease or a malignant or premalignant disease, wherein there is administered to a subject to be treated, for example a human patient or an animal, a preparation that comprises a hydroxymethyl-group-containing glycosaminoglycan in an amount sufficient to treat the disease.

Glycosaminoglycans are linear polysaccharides composed of repeating modified disaccharides. The individual disaccharide units consist of a uronic acid which is bonded 1 3 glycosidically to an amino sugar, such as N-acetyl-glucosamine. The disaccharide units of the chains themselves are linked 1 4 glycosidically. Glycosaminoglycans are constituents of many biological macromolecules and form the skeleton of many fibre-forming substances. Examples of glycosaminoglycans are hyaluronic acid, heparin, chondroitin sulfate, dermatan sulfate and keratan sulfate. According to the invention, chitosamine and poly-N-acetyl-glucosamine are additionally understood as being glycosaminoglycans. The glycosaminoglycan is preferably a hyaluronic acid.

Glycosaminoglycans are conventionally obtained from protein-containing biological tissues. It is known, for example, to isolate hyaluronic acid from cockscomb or *streptococci*. Natural heparins are extracted inter alia from intestinal mucosa of pigs. Chondroitin sulfate is for the most part obtained from cartilaginous tissue of cattle, pigs and sharks. In addition, glycosaminoglycans can be produced from genetically modified host organisms, for example bacterial cells.

In medicine, hyaluronic acid and derivatives thereof are used for the viscoelastic supplementation of joints in arthritis, for the filling of tissues, in particular of the dermis, as so-called "dermal fillers", and for the treatment of inflammatory diseases of the skin and mucosa. For example, WO 2005/067944 describes the treatment and prophylaxis of diseases of the skin and mucosa caused by herpes- and papilloma-viruses.

Surprisingly, it has now been found that glycosaminoglycan derivatives in which one or more amino groups are substituted with hydroxymethyl groups possess an anti-infective action and additionally are suitable for the treatment of malignant or premalignant diseases of body surfaces.

The disaccharide units of which glycosaminoglycans are composed consist, as mentioned above, of a uronic acid and an amino sugar. In the glycosaminoglycan derivatives substituted with hydroxymethyl groups according to the invention, a hydroxymethyl group is bonded to one or more nitrogen atoms of amino groups. The hydroxymethyl-group-containing glycosaminoglycans according to the invention accordingly have characteristic substituents —N(R)—CH$_2$OH, wherein R can be any desired radical, in particular H or acetyl. These are preferably bonded to amino sugars of the disaccharide units of the glycosaminoglycan. In the case of glycosaminoglycans that contain the amino sugar N-acetylglucosamine, the N-acetyl group is preferably substituted with a hydroxymethyl group. —N(Acetyl)-CH$_2$OH groups are characteristic of these hydroxymethyl-group-containing glycosaminoglycans within the meaning of the invention. These compounds surprisingly exhibit a particularly high anti-infective action.

Infectious diseases within the meaning of the present invention can be caused by various types of pathogens, such as in particular fungi, bacteria or viruses. In specific embodiments of the invention they are infectious diseases that are not caused by papilloma- or herpes-viruses. Examples of infectious diseases that can be treated or prevented according to the invention by means of hydroxymethyl-group-containing glycosaminoglycans are infectious diseases of the skin or mucosa. The mucosa include in particular also the surfaces of the gastrointestinal tract, of the urogenital tract, of the lungs and of hollow organs.

Particularly preferably, there can be treated by the hydroxymethyl-group-containing glycosaminoglycans infectious diseases which are primarily viral infectious diseases with subsequent superinfection by bacteria and/or fungi, preferably of species that are resistant to conventional antibiotics. The viruses are DNA and RNA viruses, the bacteria are pathogenic gram-negative and gram-positive, anaerobically or aerobically growing bacteria, and the fungi are preferably budding fungi (yeasts) and ray fungi.

The agent according to the invention is also suitable for the treatment of malignant diseases of the body surfaces, in particular of basal cell carcinoma of the epidermis and its pre-stages such as solar keratosis or Bowen's disease. This is injected, for example, with a gel-like preparation of the agent according to the invention and then grows to the surface, where it is detached. Other malignant diseases can also be treated adjuvantly with the agent according to the invention, for example peritoneal carcinomatosis by means of a solution instilled into the abdominal cavity.

Preferred examples of glycosaminoglycans used according to the invention are hyaluronic acid, heparin, chondroitin sulfate, chitosamine and poly-N-acetyl-glucosamine substituted on amino groups with hydroxymethyl, with hyaluronic acid being particularly preferred.

In the glycosaminoglycan derivatives according to the invention, one or more amino groups are substituted with hydroxymethyl groups. Preferably, the degree of hydroxymethylation is in the range from 200:1 (0.5%) to 1:1 (100%), preferably from 100:1 (1%) to 10:1 (10%). As the degree of hydroxymethylation of the glycosaminoglycans increases, the anti-infective action of glycosaminoglycans surprisingly increases. For hydroxymethyl-hyaluronic acid, it has been possible to show in vitro that the virucidal action in particular is increased. A particularly preferred embodiment of the invention is therefore hydroxymethyl-hyaluronic acid for use in the treatment or prevention of infectious diseases, in particular viral diseases, bacterial diseases or fungal diseases. In specific embodiments of the invention, these diseases are not caused by herpes- or papilloma-viruses.

In comparison with known anti-infective agents, such as, for example, taurolidine, the hydroxymethyl-group-containing glycosaminoglycans according to the invention have improved tissue tolerance. They remain at their target location for longer, it being possible to control the retention time by the choice of the molecular weight of the glycosaminoglycan used and its degree of crosslinking. For example, hydroxymethyl-hyaluronic acid, depending on its molecular weight and degree of crosslinking, remains at the target location for approximately from 24 hours to up to six months.

A further advantage is the substantially increased stability of the compounds, that is to say virtually no decomposition of the compounds with release of volatile formaldehyde. As compared with the widely used anti-infective antibiotics, the modified glycosaminoglycans according to the invention have the advantage that the pathogens do not develop resistance and the pathogen spectrum is increased. Degradation and excretion occur naturally by way of specific enzymes.

For the treatment of infectious diseases, hydroxymethyl-group-containing glycosaminoglycans within the meaning of the invention in both uncrosslinked and crosslinked form or in the form of mixtures are suitable. Particular preference is given to the use of uncrosslinked or crosslinked hyaluronic acid or mixtures thereof.

Uncrosslinked glycosaminoglycans are preferably selected from (i) long-chain glycosaminoglycans having an average molecular weight (weight average) of at least 200 kD and (ii) short-chain glycosaminoglycans having an average molecular weight (weight average) of up to 50 kD, or mixtures thereof.

Crosslinked glycosaminoglycans can be, for example, covalently or non-covalently crosslinked. The preparation of crosslinked glycosaminoglycans can take place in a manner known per se. Covalent crosslinking is generally effected by crosslinking with bifunctional reactive agents, such as, for example, diepoxyoctane, BDDE, divinylsulfone, glutaraldehyde or carbodiimide, via bifunctional amino acids, for example lysine, protamine or albumin. Crosslinking can, however, also be achieved, for example, by an amide, ester or ether bond. Further suitable reagents for the covalent crosslinking of glycosaminoglycans are ethylene glycol or 1,4-butanediol diglycidyl ether, divinylsulfone, photocrosslinking reagents such as ethyleosine, hydrazides such as bishydrazide, trishydrazide and polyvalent hydrazide compounds. It is further possible to use intra- and/or intermolecularly esterified glycosaminoglycans or glycosaminoglycans crosslinked with hexamethylenediamine. Particular preference is given to non-covalent crosslinking using polyvalent metal ions, such as, for example, iron, copper, zinc, calcium, magnesium, manganese, barium and other chelating metal ions.

Of importance for the application is the molecular weight and, in the case of crosslinked glycosaminoglycans, also the degree of crosslinking, which is, for example, in the range from 0.1 to 10%, without being limited thereto. In general it is to be noted that a lower degree of crosslinking is sufficient in the case of long-chain glycosaminoglycans to obtain a gel-like matrix, whereas in the case of short-chain glycosaminoglycans, a higher degree of crosslinking is required to obtain comparable properties.

The glycosaminoglycan according to the invention can be used both in human medicine and in veterinary medicine, for example for the treatment of domestic animals or livestock.

Administration of the hydroxymethyl-group-containing glycosaminoglycan can in principle be carried out in any desired manner, providing it is suitable for treating the particular disease in question. Systemic or local administration is conceivable. In many cases, local administration in the region of the diseased body location is carried out.

For use in the treatment of infectious diseases, a hydroxymethyl-group-containing glycosaminoglycan according to the invention can be in the form of a pharmaceutical composition in which one or more hydroxymethyl-group-containing glycosaminoglycans are present in an amount of preferably from 0.01 to 20 percent by weight, based on the pharmaceutical composition as a whole, in particular in an amount of from 0.01 to 5 percent by weight and particularly preferably in an amount of from 0.01 to 1 percent by weight.

The pharmaceutical compositions according to the invention can comprise as pharmaceutical excipients, for example, agents for adjusting the pH value, stabilising agents, antioxidants, solubilisers, agents assisting penetration, preservatives and/or gel-forming agents, as are conventionally used in such compositions. They are used in the amounts conventional in such preparations.

The pharmaceutical compositions according to the invention can optionally comprise, in addition to the hydroxymethyl-group-containing glycosaminoglycan, also one or more further pharmaceutical active ingredients which are compatible with the glycosaminoglycan derivative. Examples of further active ingredients are active ingredients for the therapy of skin diseases (dermatoses), antimycotics, antibiotics (e.g. gentamycin, vancomycin, penicillin or cephalosporin), sulfonamides, disinfectants, hormones (e.g. corticoids) and hormone derivatives (e.g. cortisol), local anaesthetics (e.g. of the lidocaine or novocaine type), vasoactive substances for vessel constriction (avoidance of bleeding), adrenaline, enzymes (such as e.g. hyaluronidase), interleukins, growth factors (e.g. EGF, PDGF or/and IGF), vitamins (e.g. vitamin D), skin care agents and/or agents for stimulating blood flow (hyperaemic agents). The further active ingredients can optionally be associated with the glycosaminoglycan, for example by covalent or non-covalent interactions.

Also of importance are additives, such as, for example, 2- or 3-valent metal ions, which can have a crosslinking and stabilising action as a result of gelate formation and which, on the other hand, can also accelerate the degradation of the active glycosaminoglycans.

In the tissue, the degradation of glycosaminoglycans takes place naturally by a large number of different enzymes or by oxygen radicals. Hyaluronic acid is degraded by hyaluronidases or oxygen radicals. Therefore, additives that have an inhibiting action on enzymes such as hyaluronidase (heparin, indometazine or/and salicylates) and those which, as so-called free radical acceptors, prevent oxidative degradation in the tissue (vitamins A, E or/and C) are further of importance.

In a particularly preferred embodiment of the invention there is used for the treatment or prevention of infectious diseases a mixture of long-chain glycosaminoglycans (200 kD) with short-chain glycosaminoglycans (e.g. hexamers of the repetitive disaccharide units or larger units up to 50 kD) or also mixtures of the aforementioned with crosslinked glycosaminoglycans. As a result of the mixing there are formed viscous injectable preparations, which are preferably introduced intradermally with injection cannulas or introduced extensively at the boundary of the dermo-epidermal junction by injection. The raising of individual wheals is also suitable according to the invention. Known local anaesthetics can be added to the injectable glycosaminoglycan preparations in order to minimise the painfulness of the injection.

A further particularly preferred embodiment are mixtures of crosslinked and uncrosslinked glycosaminoglycans.

Instead of the injection technique with cannulas, the preparations according to the invention can also be administered extremely effectively by pressure injection. This method is distinguished in that it is largely free of pain.

Further preparations of the active ingredient according to the invention are aqueous solutions or emulsions for intravenous administration or for instillation into body cavities or hollow organs.

The preparations according to the invention can further be applied topically, that is to say to the surface of the skin in the form of ointments, creams, lotions, gels, sprays, tinctures, shampoos, occlusive films. A particular form of preparation within the meaning of the invention is a dry glycosaminoglycan preparation in the form of a powder, which is used in particular for the treatment of weeping eczema. The introduction of the active ingredients in microencapsulated form or in the form of liposomes is also provided by the invention. Where mucosa of the respiratory passages are affected by an infectious disease, treatment with the hydroxymethyl-group-containing glycosaminoglycans according to the invention can also be carried out using an aerosol as an inhalation solution.

The preparation of a composition according to the invention can be carried out in a manner that is generally known and conventional per se for the preparation of such compositions. The order in which the individual constituents are mixed is generally not critical.

The nature, dose and frequency of the administration of the composition according to the invention and the properties (e.g. viscosity, degree of crosslinking, active ingredient content, etc.) are governed in particular by the nature and severity of the disease as well as by the age of the patient and the location and nature of the administration, e.g. the condition and sensitivity of the affected body locations. If the compositions according to the invention are administered in the form of topically administrable preparations, the administration generally complies with the conditions conventional for such compositions.

The nature of the treatment and the frequency of the administration are also governed in particular by the individual response of the persons to be treated. Preferably, an application of gels or solutions takes place at intervals of from several days to 1 or 2 months, in particular about 1-2 weeks.

The invention also includes mixtures of a hydroxymethyl-group-containing glycosaminoglycan with other glycosaminoglycans in crosslinked or/and uncrosslinked form. For possible combinations and crosslinking possibilities, reference is made to EP-B-0 619 737, DE-A 102 99 66 and WO 03/041723. Mixtures of hydroxymethyl-group-containing hyaluronic acid and heparin are preferred. Also preferred are mixtures of hydroxymethyl-group-containing hyaluronic acid and positively charged glycosaminoglycans such as chitosamine.

The preparation of a hydroxymethyl-group-containing glycosaminoglycan preferably comprises the steps:
(i) providing glycosaminoglycan and
(ii) substituting one or more amino groups of the glycosaminoglycan with hydroxymethyl groups.

There is used as the glycosaminoglycan starting product in step (i) preferably hyaluronic acid, heparin, chondroitin sulfate, chitosamine or poly-N-acetylglucosamine.

In a particularly preferred embodiment, the glycosaminoglycan in step (i) is isolated from a biological source or obtained by biotechnological means, in particular from cockscomb or bacteria, such as B. subtilis or streptococcal cultures.

The extraction of the glycosaminoglycan from a biological source or from bacteria can take place in the presence of formaldehyde or another hydroxymethyl group donor. The purified glycosaminoglycan from step (i) is then in the form of, for example, an aqueous solution, a precipitate or a hydrogel.

In step (ii), the glycosaminoglycan is then substituted with hydroxymethyl groups by chemical treatment. Step (ii) can be carried out together with step (i) or thereafter. Step (ii) can comprise, for example, the reaction of the glycosaminoglycan with formaldehyde or an agent that releases formaldehyde under the reaction conditions, such as, for example, taurolidine. A preferred method for introducing hydroxymethyl groups into the glycosaminoglycan (e.g. hyaluronic acid) uses taurolidine in 1-2% solution. The taurolidine solution is thereby added to the glycosaminoglycan in the ratio of 1 mg to 1 ml, and the mixture is incubated for 24 hours in a sealed vessel or under a gas atmosphere of 1-100 bar. The advantage of this procedure is that taurolidine itself is very much less toxic than formaldehyde.

The glycosaminoglycan modified with hydroxymethyl groups can then be purified in a further step (iii). Excess formaldehyde or residues of formaldehyde-releasing reagents from step (ii) are thereby removed. The purification can be carried out, for example, by precipitation with, for example, alcohols or salts, by chromatographic processes, dialysis processes, vacuum extraction and/or lyophilisation.

A further step (iv) is then optionally carried out, in which the glycosaminoglycan substituted with hydroxymethyl groups is crosslinked. In principle, the crosslinking can be carried out first, followed by the introduction of hydroxymethyl groups. The crosslinking can, as described above, be carried out according to methods known in the prior art. In a particularly preferred embodiment, crosslinking with one or more further glycosaminoglycans, which can optionally themselves be substituted on amino groups with hydroxymethyl groups, is carried out in step (iv). Examples of such further glycosaminoglycans optionally modified with hydroxymethyl groups are heparin, chondroitin sulfate, chitosamine and poly-N-acetylglucosamine.

In a further preferred embodiment of the invention, a hydroxymethyl-group-containing glycosaminoglycan is then combined with one or more further active ingredients and/or additives. Examples of such further active ingredients and additives are mentioned above.

A further aspect of the invention relates to a combination of hydroxymethyl-group-containing glycosaminoglycan with taurolidine, for example with a taurolidine solution, for example a 1-2% (w/v) taurolidine solution. Hyaluronic acid is preferably used as the glycosaminoglycan, it being possible for the molecular weight of the hyaluronic acid to be, for example, from 100,000 to 10,000,000 daltons.

A composition according to the invention can preferably be stored in gas-tight packaging, such as, for example, a glass syringe, and is distinguished by an increased anti-infective and prolonged action and by improved tissue tolerance.

A further preferred embodiment of the invention relates to a method for treating a bacterial inflammation of the knee joint, wherein the hydroxymethyl-group-containing glycosaminoglycan according to any one of claims 1 to 14 is preferably instilled as a gel or used as a flushing solution.

APPLICATION EXAMPLES

Example 1

HA obtained by fermentation from *Streptococcus equi* is dissolved in 2% taurolidine solution and maintained at 40 C for 12 hours. Excess liquid is then separated off by filtration and remaining liquid is removed by vacuum drying. The product obtained is then dissolved in physiological NaCl solution and the pH value of the solution is adjusted to 10 with 1% NaOH. BDDE is then added to a concentration of 0.2%. The batch is incubated for 4 hours at 40 C. The pH value of the batch is then adjusted to 7.4 with Na acetate, and the batch is maintained at 70 degrees Celsius for 24 hours. After cooling to room temperature, further processing of the batch to the anti-infective end product, for example eye gel, can be carried out.

Example 2

*Streptococcus equi* species are cultured in fermenters in a $CO_2$-enriched anaerobic atmosphere. When the growth or multiplication is complete, formaldehyde in concentrated form is added to the nutrient solution so that the bacteria die.

The solution is then centrifuged and the supernatant is removed. Dilute NaOH is added to the material obtained, and shaking is carried out for 4 hours. The solution is then neutralised and subjected to ultrafiltration. The solution obtained can be treated with alcohol and the dissolved HA precipitated and dried. There is thus obtained a product according to the invention, which can be processed further according to the intended application.

Example 3

100 ml of a 2% hyaluronic acid solution are mixed with 100 ml of a 2% tauroline solution, and the mixture is stored in a glass bottle with the exclusion of air. The solution can be instilled into the abdominal cavity or into the bladder as required by way of a tube or catheter system.

The invention claimed is:

1. A method for treating or preventing an infectious disease of the skin or mucosa caused by a viral infection, wherein the viral infection is caused by a papilloma virus or a herpes virus, comprising administering to a subject in need thereof an effective amount of a preparation consisting essentially of hydroxymethyl-group-hyaluronic acid as the active agent, wherein one or more amino groups are substituted with hydroxymethyl, wherein the degree of hydroxymethylation is in the range from 200:1 (0.5%) to 1:1 (100%), formulated for use in the treatment or prevention of infectious diseases, wherein the hydroxymethyl-group-containing glycosaminoglycan is prepared by a method comprising:
   (i) providing hyaluronic acid,
   (ii) substituting one or more amino groups of the hyaluronic acid with hydroxymethyl groups, and
   (iii) purifying the hydroxymethyl-group-containing hyaluronic acid and removing any formaldehyde or residues of formaldehyde-releasing reagents; and
one or more pharmaceutical excipients selected from the group consisting of an agent for adjusting the pH value, a stabilizing agent, a solubiliser, an agent which promotes penetration, a preservative and a gel forming agent, wherein the composition does not comprise taurolidine.

2. The method of claim 1, wherein the infectious disease is a disease of the skin or mucosa selected from a disease of body surfaces, of the gastrointestinal tract, of the urogenital tract or of the lungs.

3. The method of claim 1, wherein the degree of hydroxymethylation is in the range from 100:1 (1%) to 10:1 (10%).

4. The method of claim 1, wherein the hyaluronic acid in step (i) is obtained by biotechnological means.

5. The method of claim 4, wherein the hyaluronic acid in step (i) is isolated from transgenic bacteria.

6. The method of claim 5, wherein the hyaluronic acid in step (i) is isolated from *B. subtilis* or *streptococcal* cultures.

7. The method of claim 1, wherein the hydroxymethyl group-containing hyaluronic acid has —N(R)—$CH_2OH$ residues, wherein R=H or acetyl.

8. The method of claim 1, wherein the viral infection is caused by a papilloma virus.

9. The method of claim 1, wherein the hydroxymethyl-group-containing hyaluronic acid is formulated for local administration.

10. The method of claim 1, wherein the hydroxymethyl-group-containing hyaluronic acid is formulated for intradermal administration, for administration at the boundary of the dermo-epithelial junction or for topical administration.

11. The method of claim 1, wherein the hydroxymethyl-group-containing hyaluronic acid is present in uncrosslinked form.

12. The method of claim 1, wherein the hydroxymethyl-group-containing hyaluronic acid is selected from the group consisting of
(i) long-chain hyaluronic acids having an average molecular weight (weight average) of at least 200 kD and
(ii) short-chain hyaluronic acids having an average molecular weight (weight average) of up to 50 kD,
or mixtures thereof.

13. The method of claim 1, wherein the hydroxymethyl-group-containing hyaluronic acid is present in crosslinked form.

14. The method of claim 13, wherein the degree of crosslinking is in the range from 0.1% to 10%.

15. The method of claim 1, wherein the hydroxymethyl-group-containing hyaluronic acid is present in the form of a mixture of uncrosslinked and crosslinked hyaluronic acids.

16. The method of claim 1, wherein the hydroxymethyl-group-containing hyaluronic acid is formulated as an injectable preparation, ointment, cream, lotion, gel, spray, tincture, flushing or infusion solution, drip solution, shampoo, occlusive film, powder or inhalable preparation.

17. A method for treating or preventing an infectious disease of the skin or mucosa caused by a viral infection, wherein the viral infection is caused by a papilloma virus or a herpes virus, comprising administering to a subject in need thereof an effective amount of a preparation consisting essentially of a hydroxymethyl-group-containing hyaluronic acid as the active agent, wherein one or more amino groups are substituted with hydroxymethyl, wherein the degree of hydroxymethylation is in the range from 200:1 (0.5%) to 1:1 (100%), wherein the hydroxymethyl-group-containing hyaluronic acid is prepared by a method comprising:
(i) providing hyaluronic acid,
(ii) substituting one or more amino groups of the hyaluronic acid with hydroxymethyl groups, and
(iii) purifying the hydroxymethyl-group-containing hyaluronic acid and removing any formaldehyde or residues of formaldehyde-releasing reagents,
in combination with at least one inhibitor of hyaluronic acid degradation; and one or more pharmaceutical excipients selected from the group consisting of an agent for adjusting the pH value, a stabilizing agent, a solubiliser, an agent which promotes penetration, a preservative and a gel forming agent, formulated for use in the treatment or prevention of a viral infection of the skin or mucosa, wherein the composition does not comprise taurolidine.

18. The method of claim 16, wherein the inhalable preparation is an aerosol.

* * * * *